United States Patent [19]

Robins et al.

[11] Patent Number: 4,461,891

[45] Date of Patent: Jul. 24, 1984

[54] 2-β-D-RIBOFURANOSYLTHIAZOLE-4-CARBOXAMIDINE COMPOUNDS

[75] Inventors: Roland K. Robins, Provo, Utah; Prem C. Srivastava, Oak Ridge, Tenn.

[73] Assignee: Brigham Young University, Provo, Utah

[21] Appl. No.: 471,395

[22] Filed: Mar. 2, 1983

[51] Int. Cl.³ .............................................. C07H 19/24
[52] U.S. Cl. ........................................ 536/55; 536/53; 424/180
[58] Field of Search .................... 536/55, 53, 28, 29; 424/180

[56] References Cited

U.S. PATENT DOCUMENTS

Re. 29,835  11/1978  Witkowski et al. ................. 536/29

OTHER PUBLICATIONS

Fuertes et al., *Journal of Organic Chemistry*, 1976, vol. 41, No. 29, pp. 4074–4077.

Srivastava et al., *Journal of Medicinal Chemistry*, 1977, vol. 20, No. 2, pp. 256–262.

*Primary Examiner*—Johnnie R. Brown
*Assistant Examiner*—Elli Peselev
*Attorney, Agent, or Firm*—Krass & Young

[57] ABSTRACT

2-β-D-Ribofuranosylthiazole-4-carboxamidine (I) and salts are provided as well as a means for their production and use. The compounds typically show unique pharmacological activity, especially antienzyme and cytotoxic activity.

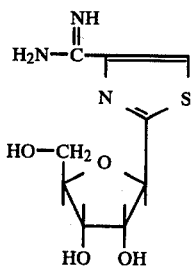

2 Claims, No Drawings

2-β-D-RIBOFURANOSYLTHIAZOLE-4-CARBOXAMIDINE COMPOUNDS

DESCRIPTION

TECHNICAL FIELD

This invention is directed to 2-β-D-ribofuranosylthiazole-4-carboxamidine compounds which are found to have unique pharmacological activity, especially antienzyme activity and cytotoxic activity, and means for their production.

SUMMARY AND DETAILED DESCRIPTION

The present invention in one preferred embodiment relates to 2-β-D-ribofuranosylthiazole-4-carboxamidine (I) having the formula:

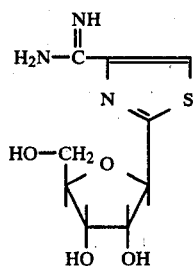

and pharmaceutically acceptable salts thereof such as the hydrochloride salt. The compounds of the invention advantageously possess a carbon-to-carbon bond at the 2-position and thereby resist cleavage unlike nitrogen-to-carbon linked compounds such as are described in U.S. Pat. No. 3,798,209.

The invention in another preferred aspect relates to a process for the production of ribofuranosylthiazole-4-carboxamidine compounds. The process comprises subjecting a 2-(2,3,5,-tri-O-acyl-β-D-ribofuranosyl)-thiazole-4-carbonitrile to ammonolysis and isolating the 2-β-D-ribofuranosylthiazole-4-carboxamidine in salt or non-salt form.

The ammonolysis reaction, for the production of 2-β-D-ribofuranosylthiazole-4-carboxamidine is preferably carried out in the presence of ammonium chloride to provide the carboxamidine in the form of its hydrochloride salt. Other pharmaceutically or physiologically acceptable acid addition salts (e.g., hydrobromic, hydroiodic, citric, acetic, sulfuric, and phosphoric acid addition salts) may be obtained from the hydrochloride by suitable means such as ion exchange or by neutralization of the hydrochloride with a base such as sodium bicarbonate and reaction of the free carboxamidine with an appropriate acid. The product is isolated from the reaction mixture in any suitable way such as by column chromatography. The acyl groups of the starting material can be varied widely since they are removed in the reaction and thus their choice is not critical. Preferred acyl groups are acetyl, n-butyryl, and benzoyl.

The compound 2-β-D-ribofuranosylthiazole-4-carboxamidine as the hydrochloride salt has been shown to exhibit significant antienzyme activity and cytotoxic activity. In particular, the compound, in a standard protocol, patterned after that reported in Biomedicine, 33, 39–41(1980), has been shown typically to inhibit the formation of [$^{14}$C]-hypoxanthine from [$^{14}$C]-inosine using human erythrocytes as the source of enzyme. In the test, known as the purine nucleoside phosphorylase (PNP-4) test, total inhibition was achieved at a concentration less than about 300 micromoles. The compound also was found by a standard test (Science, 214, 1137, 1981) to be selectively cytotoxic for T-cells in the presence of 2'-deoxyguanosine. Since T-cells play a central role in immune response, use of the compounds of the invention is contemplated for the immunoregulation of autoimmune disease such as rheumatoid arthritis, systemic lupus erythematosus, and inflammatory bowel disease. The present invention in another preferred aspect therefore relates to compositions containing at least one compound of the invention in treating disease such as autoimmune disease characterized by abnormal immune response in warm blooded animals. According to this aspect of the invention, the properties of 2-β-D-ribofuranosylthiazole-4-carboxamidines are utilized by administering to a warm blooded animal an effective amount of a pharmaceutical composition containing as the active ingredient at least about 0.1 percent by weight, based on the total weight of the composition of at least one such compound of the invention.

Pharmaceutical compositions of the invention can be formulated in any suitable way, preferably with an inert carrier. Preferably, the pharmaceutical carrier is chosen to allow administration of a suitable concentration of the composition of the invention as a solution or suspension by injection into an afflicted warm blooded animal. Administration may be intravenous, intramuscular, intracerebral, subcutaneous, or intraperitoneal.

Alternatively, the composition of the invention may be formulated in an appropriate pharmaceutical carrier allowing for administration by another route such as oral, ophthalmic, topical or by suppository.

The invention and the best mode of carrying out the same are described in the following illustrative examples.

EXAMPLE 1

2-β-D-Ribofuranosylthiazole-4-Carboxamidine, hydrochloride

A mixture of 2-(2,3,5-tri-O-acetyl-β-D-ribofuranosyl)-thiazole-4-carbonitrile (17 g, 46 mmol; J. Med. Chem. 20, 256, 1977), ammonium chloride (2.46 g, 46 mmol) and liquid ammonia (150 ml) was placed in a stainless steel pressure vessel and heated at 105 degrees for 4 hours. The ammonia was vented and the residue coevaporated two times with methanol. The residue was dissolved in methanol and the red solution adsorbed on silica gel (20 g). The resulting powder was slurried in chloroform and placed on a silica gel column (200 g packed in chloroform). Elution with chloroform:methanol (4:1) provided, after evaporation of the pooled fractions containing a single TLC spot, 9.1 g (67%) of pink foam. Recrystallization of this material from methanol:acetonitrile (charcoal) afforded 6.5 g (47%) of the amidine hydrochloride from 3 crops as faintly pink crystals, mp 205–206 degrees d. after drying at 100 degrees, 0.05 torr, for 3 hours; nmr (DMSO-$d_6$): 5.17 ppm (d, 1, $\underline{H_1}$·J=1 Hz) 8.99 (s, 1, C$_5\underline{H}$); [α]D optical rotation, −2.08° (c, 1.15% $H_2O$).

In the T-cell test, the hydrochloride salt with 2'-deoxyguanosine (10 micromoles) was found to be toxic for T-lymphoblasts at the following ED$_{50}$ micromolar doses: ca 77 (CEM T-lymphoblasts), ca 27 (MOLT-4), and ca 7 (HSB).

The following representative Examples 2 through 6, are given as illustrative pharmaceutical compositions utilizing different carriers. In these examples, Example 2 illustrates the use of the compounds of the invention in injectables suitable for intravenous or other types of injection into the host animal. Example 3 is directed to an oral syrup preparation, Example 4 to an oral capsule preparation and Example 5 to oral tablets. Example 6 is directed to use of the compounds of the invention in suitable suppositories. For example 2 through 6, the ingredients are listed followed by the methods of preparing the composition.

EXAMPLE 2

INJECTABLE

COMPOUND OF EXAMPLE 1: 125 mg–500 mg
Water for Injection USP q.s.

COMPOUND is dissolved in the water and passed through a 0.22 micron filter. The filtered solution is added to ampoules or vials, sealed and sterilized.

EXAMPLE 3

SYRUP

250 MG Active ingredient/5 ml syrup
COMPOUND of Example 1: 25 g
Purified Water USP: 200 ml
Cherry Syrup q.s. or: 1000 ml COMPOUND is dissolved in the water and to this solution the syrup is added with mild stirring.

EXAMPLE 4

CAPSULES 50 mg, 125 mg or 250 mg
COMPOUND of Example 1: 500 g
Lactose USP, Anhydrous q.s. or: 200 g
Sterotex Powder HM: 5 g Combine COMPOUND and the Lactose in a twin-shell blender equipped with an intensifier bar. Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filed with 141 mg. 352.5 mg or 705 mg of the blend, respectively, for the 50 mg., 125 mg and 250 mg containing capsules.

EXAMPLE 5

TABLETS 50 mg, 100 mg or 250 mg
COMPOUND of Example 1: 250 g
Corn Starch NF: 200.0 g
Cellulose, Microcrystalline: 46.0 g
Sterotex Powder HM: 4.0 g
Purified Water q.s. or 300.0 ml Combine the cornstarch, the cellulose and COMPOUND together in a planetary mixer and mix for two minutes. Add the water to this combination and mix for one minute. The resulting mix is spread on trays and dried until a moisture level of 1 to 2 percent is obtained. The dried mix is then milled with a Fitzmill through a #RH 2B screen at medium speed. The Sterotex Powder is added to a portion of the mix and passed through a #30 screen, and added back to the milled mixture and the total blended for five minutes by drum rolling. Compressed tablets of 150 mg. 375 mg and 750 mg respectively, of the total mix are formed with appropriate sized punches for the 50 mg, 125 mg or 500 mg containing tablets.

EXAMPLE 6

| 125 mg. 250 mg or 500 mg per 3 g | | | |
|---|---|---|---|
| COMPOUND of Example 1 | 125 mg | 250 mg | 500 mg |
| Polyethylene Glycol 1540 | 1925 mg | 1750 mg | 1400 mg |
| Polyethylene Glycol 8000 | 825 mg | 750 mg | 600 mg |

Melt the Polyethylene Glycol 1540 and the Polyethylene Glycol 8000 together at 60 degrees C. and dissolve COMPOUND into the melt. Mold this total at 25 degrees C. into appropriate suppositories.

Having thus described our invention, what is desired to claim as our exclusive privilege and property is the following:

1. 2-β-D-ribofuranosylthiazole-4-carboxamidine and pharmaceutically acceptable salts thereof.

2. A compound according to claim 1 which is 2-β-D-ribofuranosylthiazole-4-carboxamidine, hydrochloride.

* * * * *